(12) United States Patent
Espinoza et al.

(10) Patent No.: US 6,403,660 B1
(45) Date of Patent: Jun. 11, 2002

(54) PRODUCTION OF HYDROCARBONS

(75) Inventors: Rafael L. Espinoza, Sasolburg (ZA);
Jesus M. Santamaria, Zaragoza (ES);
Miquel A. Menendez, Zaragoza (ES);
Joaquin Coronas, Zaragoza (ES);
Silvia Irusta, Santa Fe (AR)

(73) Assignee: Sasol Technolgy (Proprietary) Limited, Johannesburg (ZA)

( * ) Notice: Subject to any disclaimer, the term of this patent is extended or adjusted under 35 U.S.C. 154(b) by 0 days.

(21) Appl. No.: 09/730,472

(22) Filed: Dec. 5, 2000

Related U.S. Application Data

(63) Continuation of application No. PCT/IB99/01043, filed on Jun. 7, 1999.

(30) Foreign Application Priority Data

Jun. 11, 1998 (ZA) ............................................. 98/5093

(51) Int. Cl.$^7$ ............................................. C07C 27/00
(52) U.S. Cl. ...................................................... 518/700
(58) Field of Search ........................................ 518/700

(56) References Cited

FOREIGN PATENT DOCUMENTS

EP 0609079 8/1994

OTHER PUBLICATIONS

Huff, Gedne A. et al "Intrinsic Kinetics of the Fischer–Tropsch Synthesis on a Reduced Fused–Magnetite Catalyst." Ind. Eng. Chem. Process Des. Dev., vol. 23, No. 4(1984) pp 696–705.

Yates, Ian C. et al "Intrinsic Kinetics of Fischer–Tropsch Synthesis on a Cobalt Catalyst" Energy & Fueles, vol. 5 No. 1 (1991) pp 168–173.

Salomon, Miguel et al. Synthesis of a mordenite/ZSM–5/chabazite hydrophilic membrane on a tubular support. Application to the separation a water–propanol mixture Chem. Commun. (1997/pp1–3).

Emmett, Paul H., Catalysis, vol. IV (N.Y. Reinitold) 1961 pp 258–296.

Duvenhage, Dawid J., "An Investigation of the Physical and Chemical Changes Occurring in a Fischer–Tropsch Fixed Bed Catalyst During Hydrocarbon Synthesis". From a Thesis submitted to the Faculty of Science, Univ. of Witwaterstrand, Johannesburg, (1990) pp 45–57.

*Primary Examiner*—Johann Richter
(74) *Attorney, Agent, or Firm*—Ladas & Parry

(57) ABSTRACT

A process for producing hydrocarbons involves allowing reactants forming part of a reaction medium in a reaction zone, to react at reaction conditions so as to form primary hydrocarbon products. Water is formed as a by-product. The by-product water, on formation under the reaction conditions, is allowed to permeate through a porous membrane, thereby to be separated from the reaction medium.

10 Claims, 6 Drawing Sheets

PRODUCTION OF HYDROCARBONS

This application is a Continuation of PCT/IB99/01043 filed on Jun. 7, 1999.

THIS INVENTION relates to the production of hydrocarbons. It relates in particular to a process and a reactor for producing hydrocarbons.

According to a first aspect of the invention, there is provided a process for producing hydrocarbons, which process comprises allowing reactants forming part of a reaction medium in a reaction zone, to react at reaction conditions so as to form primary hydrocarbon products, with water being formed as a by-product; and allowing by-product water, on formation thereof under the reaction conditions, to permeate through a membrane capable of selectively removing water from the reaction medium, thereby to be separated from the reaction medium.

The reactants may be in gaseous form. The reactants may, in particular, comprise carbon monoxide and hydrogen, with a particulate Fischer-Tropsch catalyst also forming part of the reaction medium. The reaction conditions will thus be selected such that the carbon monoxide and hydrogen react in the presence of the Fischer-Tropsch catalyst, to produce, as the primary hydrocarbon products, liquid Fischer-Tropsch derived hydrocarbon product(s), and/or gaseous Fischer-Tropsch derived product(s), in accordance with a simplified Fischer-Tropsch reaction equation (1):

$$CO+(1+x)H_2 \rightarrow CH_{2x}+H_2O \qquad (1)$$

The process may include continuously feeding a synthesis gas comprising the carbon monoxide and hydrogen into the reaction zone where the Fischer-Tropsch reaction takes place, while thus maintaining the reaction zone at typical Fischer-Tropsch operating conditions.

The reaction zone may be provided by a slurry bed reactor or by a fluidized bed reactor. In the case of a slurry bed reactor, the slurry bed thereof will comprise liquid hydrocarbon products, gaseous hydrocarbon products, water, synthesis gas, and catalyst particles. In the case of a fluidized bed reactor, the fluidized bed thereof will comprise gaseous hydrocarbon products, synthesis gas, water, and catalyst particles. The membrane is thus located in the slurry or fluidized bed so that by-product water can be removed as it is formed in accordance with equation (1). The reaction medium thus comprises, in the case of the slurry bed reactor, the liquid hydrocarbon products, the gaseous hydrocarbon products, water, synthesis gas and the catalyst particles. In the case of the fluidized bed reactor, the reaction medium comprises the gaseous hydrocarbon products, synthesis gas, water, and the catalyst particles.

The synthesis gas thus enters the reaction zone of the reactor at a low level below, or at the bottom of, the slurry or fluidized bed. The liquid hydrocarbon products are withdrawn from the bed through a liquid product outlet, in the case of the slurry bed reactor, while the gaseous hydrocarbon products are withdrawn from the top of the reaction zone, in the case of the slurry and fluidized bed reactors.

The Fischer-Tropsch catalyst may be iron-based, cobalt-based, or iron- and cobalt-based. It is, as hereinbefore described, in particulate form.

The temperature in the reaction zone may be between 160° C. and 380° C., typically about 200° C. to 250° C. in a slurry bed reactor, and typically about 300° C. to 360° C. in a fluidized bed reactor. The pressure may be between 1800 kPa(a) and 5000 kPa(a), typically about 2000 kPa(a) to 4500 kPa(a).

Water is thus, as is evident from equation (1), one of the main products of the Fischer-Tropsch reaction, in addition to the primary products, ie in addition to the hydrocarbons.

It is also evident from equation (1) that the higher the per pass ($H_2$+CO) conversion, the higher the partial pressure of water inside the reactor.

Although it is a product from the Fischer-Tropsch reaction, water has unfavourable or negative effects on the Fischer-Tropsch catalyst.

These unfavourable or negative effects of water, in the case of an iron-based Fischer-Tropsch catalyst, include the water decreasing the Fischer-Tropsch reaction rate; the water reoxidizing, and hence deactivating, the catalyst; and, in the case of a precipitated iron-based catalyst, the water lowering the mechanical strength of the catalyst particles. In the case of a cobalt-based catalyst, reaction water also causes reoxidation, and hence deactivation, of the catalyst; and, in the case of a precipitated cobalt-based catalyst, the water lowers the mechanical strength of the catalyst particles.

These unfavourable effects are thus avoided or at least reduced by removing by-product or reaction water from the reaction medium by means of the membrane, in accordance with the invention.

Additionally, in a slurry or fluidized bed Fischer-Tropsch reactor, alongside the (principle) Fischer-Tropsch reaction in accordance with equation (1), there occurs a reversible water-gas shift (WGS) reaction, in accordance with equation (2):

$$CO+H_2O \leftrightarrows CO_2+H_2 \Delta H=-41.1 \text{ kJ/mol} \qquad (2)$$

According to the present invention, water is continuously removed from the reaction medium as it is produced by the Fischer-Tropsch reaction. Accordingly, the water partial pressure decrease has a direct influence on the WGS reaction, in a sense that, in equation (2) the equilibrium shifts to the left, following the well-known Le Chatelier's principle.

This results in some unexpected advantages, viz undesired CO consumption in the WGS reaction is thus inhibited so that more CO is available for reaction in the Fischer-Tropsch reaction, thus improving the carbon (monoxide) consumption efficiency of the process, the equilibrium shift to the left, in equation (2), results in an overall decrease in the $H_2O/CO$ ratio in the reaction medium, which translates into an increase in the selectivity potential of the Fischer-Tropsch reaction towards desired unsaturated hydrocarbons and oxygenated chemicals, eg carbonyls, rather than paraffins; and a lower $H_2/CO$ ratio results in an increase in the α-value (the chain-grown probability factor).

The membrane may be supported by a water-permeable, eg porous, support such that the membrane has a water inlet side or surface and a water outlet side or surface, with the by-product water thus entering the membrane through its water inlet side or surface, permeating through the membrane, and exiting the membrane through its water outlet side or surface. The support and the membrane thus form a water separation device.

The process may include passing an inert sweep gas along the support in proximity to the water outlet side of the membrane, to entrain water which permeates through the membrane, thereby to provide a driving force for water permeation through the membrane.

The separation device may be of any suitable shape or configuration, eg it may be of tubular shape, and may then be of elongate form, U-shaped, or of an other suitable form or configuration. The separation device may be oriented at any suitable inclination, eg the separation device, or the major components thereof such as its limbs when it is U-shaped, may be located horizontally, vertically, or at an angle to the vertical.

When the support is of tubular form, the membrane may be provided on the inner or on the outer surface of the tubular support, with the sweep gas passing through the inside of the membrane. Thus, the sweep gas may enter the reaction zone through a conduit connected to the inside of the tubular support at or near one end thereof, pass through the support, and exit the reaction zone through another conduit leading from the support at or near another end thereof, out of the reaction zone. In this fashion, the sweep gas is thus not exposed to the reaction medium. The sweep gas may be any suitable inert gas such as nitrogen, synthesis gas, or the like.

While the membrane can, at least in principle, be of any suitable material capable of selectively removing water from the reaction medium such as of polymeric material, it may, in particular, be of zeolitic material, ie it may be zeolite-based.

Any suitable zeolite capable of selectively removing water from the reaction medium may, at least in principle, be used for the zeolite based or zeolitic membrane. Thus, the zeolite may be selected from mordenite, ZSM-5, zeolite A, or chabazite; however, mordenite is preferred.

The support may be of any suitable water-permeable material having sufficient strength to support the membrane, such as a porous metal eg stainless steel, a ceramic eg alpha or gamma alumina, a multichannel support, or the like; however, porous stainless steel is preferred.

The thickness of the membrane will depend primarily on the preparation procedure of the separation device, and on the pore size of the support employed. Typically, the membrane thickness may be in the range of 5 to 30 microns, ie micrometers. It is believed that the membrane thickness will affect both the permeation flux and the probability of defects occurring in the membrane.

The support may have a thickness of from 1 to 2 mm, and may have pores in the range of 5 nanometers to 500 nanometers. Thus, in one embodiment of the invention, the support may be of porous stainless steel having pores of about 500 nanometers, eg as obtainable from Mott Metallurgical Co. In another embodiment of the invention, the support may be of porous gamma-alumina having pores of about 5 nanometers, eg as obtainable from Societe des Ceramiques Techniques. In yet another embodiment of the invention, the support may be of porous gamma-alumina having pores of about 60 nanometers, eg as obtainable from Inocermic. In still another embodiment of the invention, the support may be of porous alpha-alumina having pores of about 200 nanometers, eg as obtainable from Societe des Ceramiques Techniques.

The Applicant has surprisingly found that the water permeation rate as well as the selectivity for the removal of water strongly depend on the temperature and on the partial pressure of water in the reaction zone. High selectivities and high water permeation fluxes occur at the high reaction temperatures and high water partial pressures. Selectivity also increases with an increase in the molecular weight of the hydrocarbons that are formed.

The invention has the advantages of improving the productivity of the Fischer-Tropsch process, and the lifetime of iron and cobalt based Fischer-Tropsch catalysts. The zeolite based membrane that is used in this invention is capable of selectively extracting the reaction water from the Fischer-Tropsch reaction medium with high (water/species i) separation factors, with species i being, for example, hydrocarbons, CO, $CO_2$ or $H_2$. This occurs even under relatively low partial pressures of water.

According to a second aspect of the invention, there is provided a reactor for producing hydrocarbons, which comprises a reactor vessel having a catalyst bed zone which, in use, will contain a slurry or fluidized bed of catalyst particles suspended or fluidized in liquid and/or gaseous hydrocarbon product;

a gas inlet in the vessel at a low level within the catalyst bed zone, for introducing gaseous reactants into the vessel;

a gas outlet in a head space of the vessel above the catalyst bed zone, for withdrawing unreacted gaseous reactants and gaseous products from the vessel; and a membrane capable of selectively removing water from a reaction medium, located in the catalyst bed zone so that any by-product water which is formed in the reaction zone on reaction of the gaseous reactants to form the liquid and/or gaseous hydrocarbon product, can permeate through the membrane.

As hereinbefore described, the membrane may be supported by a water-permeable support such that the membrane has a water inlet side or surface and a water outlet side or surface, with the by-product water thus, in use, entering the membrane through its water inlet side; permeating through the membrane, and exiting the membrane through its water outlet side. The support and the membrane may thus form a water separation device, as hereinbefore described.

The support may, in particular, be of tubular form having a central passageway, with the membrane being provided on the inner or the outer surface of the tubular support. A sweep gas feed conduit may be connected to one end of the central passageway of the tubular membrane, for feeding an inert sweep gas into and along the central passageway of the membrane, with a sweep gas withdrawal conduit leading from the other end of the membrane central passageway.

The reactor may, in particular, be a slurry or fluidized bed reactor as hereinbefore described. The reactor may still more particularly be used for producing hydrocarbons by means of a Fischer-Tropsch reaction, using a Fischer-Tropsch catalyst, as hereinbefore described.

The invention will now be described in more detail with reference to the accompanying drawings and non-limiting examples.

BRIEF DESCRIPTION OF DRAWINGS

Referring to FIG. 1, reference numeral 10 generally indicates a slurry bed Fischer-Tropsch reactor in which a process for producing hydrocarbons, in accordance with one embodiment of the invention, can be carried out.

Figure 1:
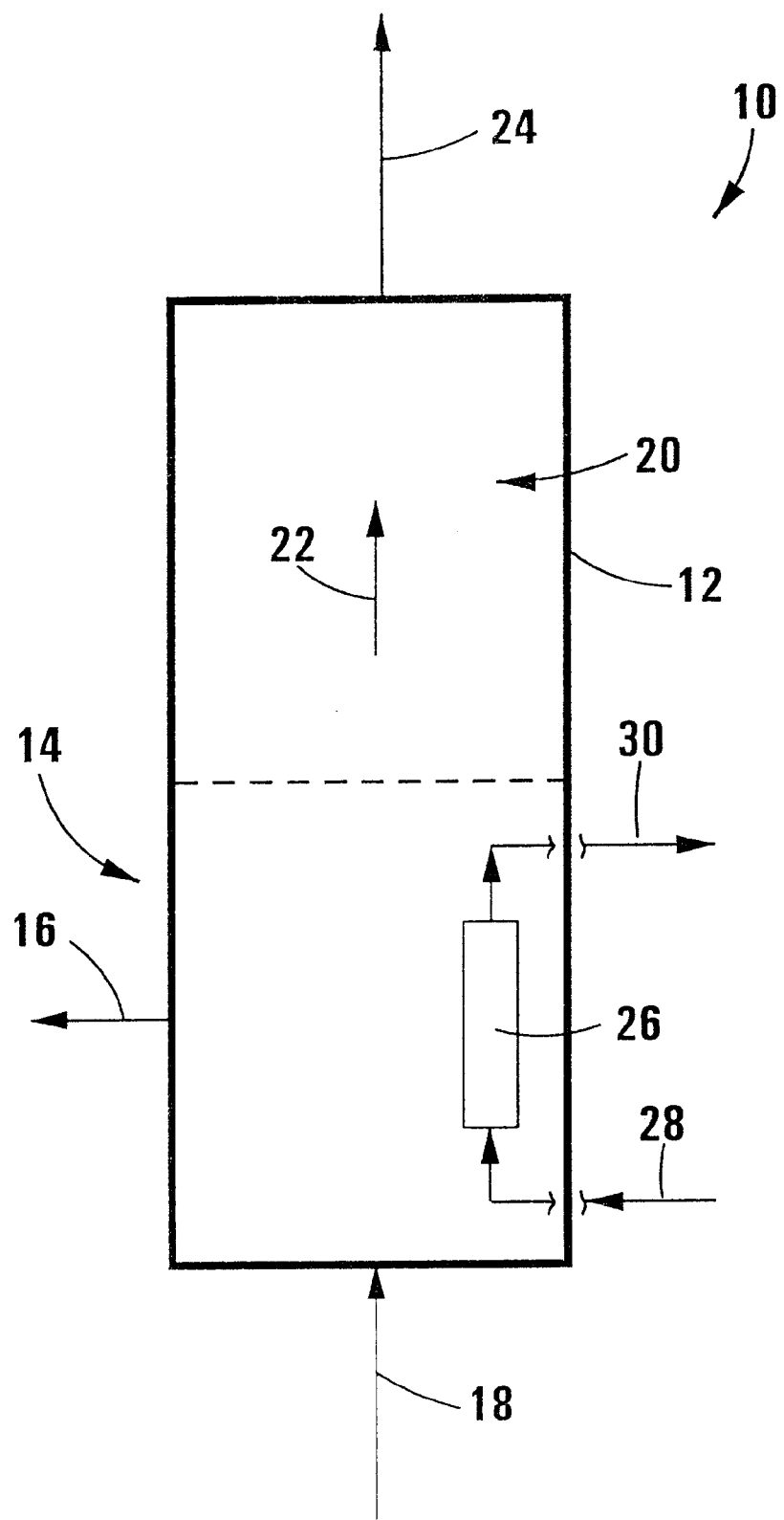
FIG. 1 shows, schematically, a reactor according to one embodiment of the second aspect of the invention.

The reactor 10 includes a Fischer-Tropsch reactor vessel 12 having, in the lower portion thereof, a slurry bed zone 14. In use, the slurry bed zone 14 will contain a slurry bed comprising cobalt or iron-based Fischer-Tropsch catalyst particles suspended in liquid and gaseous hydrocarbon products. A liquid Fischer-Tropsch derived hydrocarbon product withdrawal line 16 leads from the vessel 12 within the slurry bed zone 14. The vessel 12 also contains, in the slurry bed zone 14, cooling coils (not shown).

A synthesis gas feed line 18 leads into the vessel 12, at the bottom of the slurry bed zone 14. Synthesis gas thus, in use, enters the bottom of the slurry bed 14 through a gas distributor (not shown).

The vessel 12 also has a head space 20 above the slurry bed zone 14 and which, in use, will contain gaseous Fischer-Tropsch derived products and unreacted synthesis gas which will move upwardly through the head space 20 in the direction of the arrow 22.

A gaseous product withdrawal line 24 leads from the vessel 12, at the top of the head space 20.

A tubular separation device 26 is located uprightly within the slurry bed zone 14. The separation device 26 comprises a tubular support of porous stainless steel or porous alpha alumina, with a zeolite membrane located against, eg applied to, the inner or the outer surface of the support so that it is supported by the support. It will be appreciated that more than one of the separation devices 26 will normally be provided. A sweep gas feed conduit 28 leads into the vessel 12 and is attached to the lower inlet end of the central passageway of the tubular support of the separation device 26. A sweep gas withdrawal conduit 30 is attached to the other upper end of the central passageway of the tubular support and leads out of the vessel 12.

In use, synthesis gas comprising carbon monoxide and hydrogen enters the slurry bed zone 14 through the flow line 18 and reacts, at elevated temperature and pressure conditions which prevail within the vessel 12, to produce, under the influence of the Fischer-Tropsch catalyst in the zone 14, hydrocarbons and by-product water in accordance with equation (1) hereinbefore set out. Typically, the temperature in the vessel 12 may be about 200° C. to 250° C., while the pressure may be about 20 to 45 bar, ie 2000 to 4500 kPa.

The hydrocarbon products that are formed are in both gaseous and liquid form. The liquid hydrocarbon products are withdrawn along the flow line 16, while the gaseous hydrocarbon products pass upwardly through the head space 22 and are withdrawn along the flow line 24.

The outer surface of the tubular support of the separation device 26 is thus in contact with a reaction medium comprising liquid hydrocarbon products, gaseous hydrocarbon products, synthesis gas and catalyst particles. In order to eliminate or reduce the by-product water that is formed in the reaction medium, an inert sweep gas, typically nitrogen or synthesis gas, passes through the inside of the separation device 26 and along the flow lines 28, 30. The by-product water passes through the porous support and enters the water inlet side or surface of the membrane which is in contact with the support. The water permeates through the membrane to the water outlet side or surface thereof. The sweep gas entrains the water which passes through the membrane and collects on the inner or water outlet surface of the membrane. Water permeates through the zeolitic membrane at a substantially greater rate than does the liquid or gaseous hydrocarbon products or the unreacted synthesis gas so that the water is thereby effectively removed from the reaction medium as it is formed. The water which is thus removed naturally exits the vessel 12 with the sweep gas, along the line 30.

Figure 2:
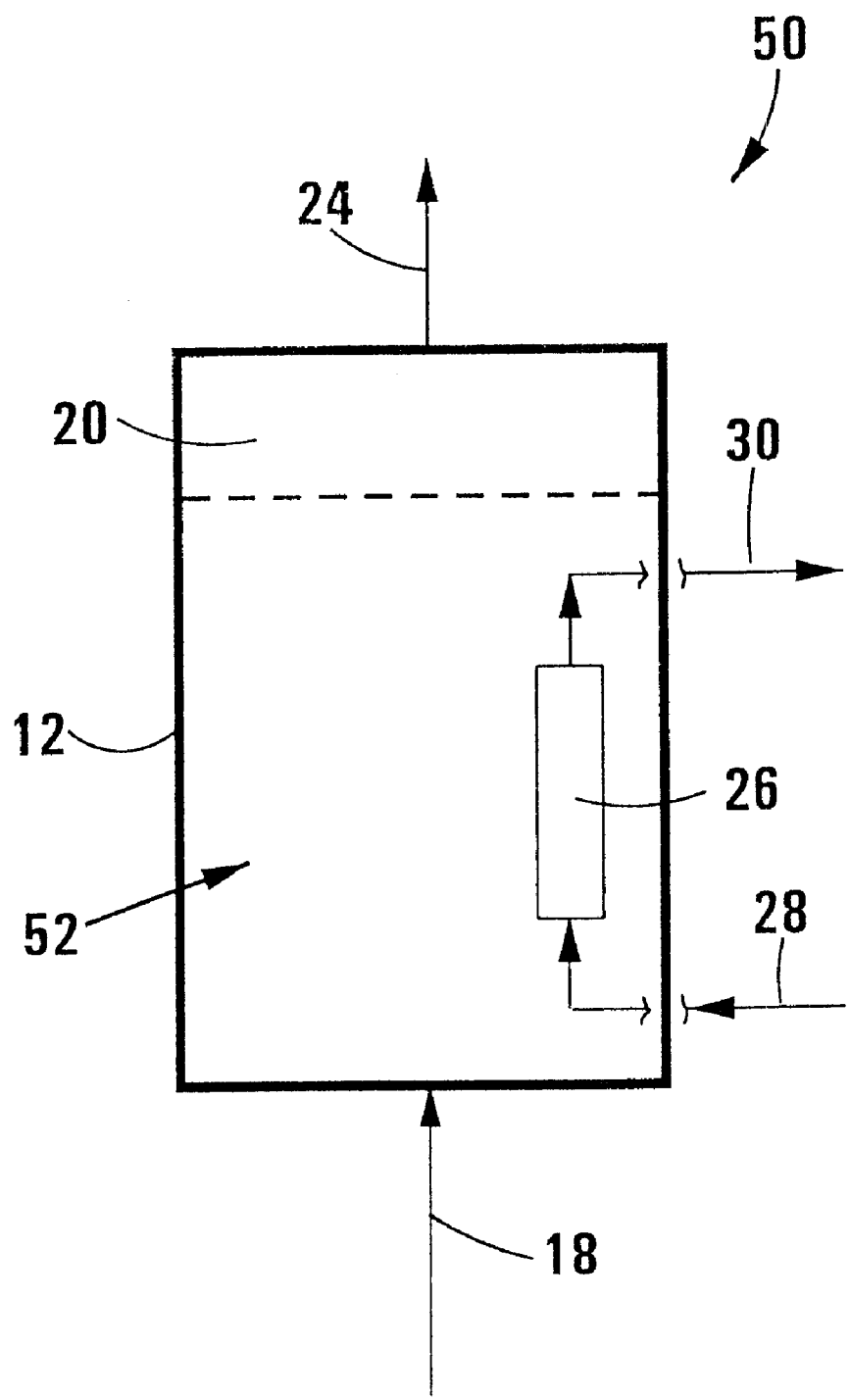
FIG. 2 shows, schematically, a reactor according to another embodiment of the second aspect of the invention.

Referring to FIG. 2, reference numeral 50 generally indicates a fluidized bed Fischer-Tropsch reactor in which a process for producing hydrocarbons, in accordance with the invention, can be carried out.

Parts of the reactor 50 which are the same as, or similar to, those of the reactor 10 hereinbefore described with reference to FIG. 1, are indicated with the same reference numerals.

The Fischer-Tropsch reactor vessel 12 of the reactor 50 includes, in a lower portion thereof, a fluidized bed zone 52, with the head space 20 provided above the fluidized bed zone 52. The separation device 26 is located in the fluidized bed zone 52.

In use, cobalt- or iron-based Fischer-Tropsch catalyst particles are fluidized by the upward flow of synthesis gas entering through the feed line 18, and gaseous products from the Fischer-Tropsch reaction, to provide a fluidized bed of the catalyst particles in the fluidized bed zone 52. The gaseous Fischer-Tropsch products and unreacted synthesis gas are withdrawn from the reactor vessel 12 via a cyclone (not shown) through the withdrawal line 24. There are no liquid hydrocarbon products at the operating conditions which prevail in vessel 12.

Thus, synthesis gas comprising mainly carbon monoxide and hydrogen enters the fluidized bed zone 52 through the flow line 18 and reacts, at elevated temperature and pressure conditions which prevail within the vessel 12, to produce, under the influence of the Fischer-Tropsch catalyst in the zone 52, hydrocarbons and water, in accordance with the simplified equation (1) hereinbefore set out. Typically, the temperature in the vessel 12 may be about 270° C. to 360° C., while the pressure may be about 15 to 45 bar, ie about 1500 to 4500 kPa.

The outer surface of the separation device 26 is thus in contact with a reaction medium comprising gaseous products from the Fischer-Tropsch reaction, synthesis gas and catalyst particles. As hereinbefore described, in order to eliminate or reduce the reaction water that is formed in the reaction medium, the inert sweep gas, typically nitrogen, passes through the inside of the tubular separation device 26 and along the flow lines 28, 30. This sweep gas entrains water which passes through the membrane and collects on the inner surface of the tubular member.

While substantially all of the by-product or reaction water can be removed in the reactors 10, 50, it will be appreciated that, in practice, the proportion of water removed may be less than 100% of the reaction or by-product water that is formed in accordance with equation (1).

Instead of using nitrogen as the sweep gas, synthesis gas or a gaseous mixture comprising mainly synthesis gas ($H_2$ and CO) but also containing some other constituents such as $CO_2$ and/or light hydrocarbons, can be used. By-product water thus entrained by the synthesis gas or synthesis gas mixture will then have to be removed before the synthesis gas is fed to the reactors 10, 50.

EXAMPLE 1

This example illustrates, on laboratory scale, the operation of the process according to the invention. It shows the manner in which a mordenite membrane material may be applied under reaction conditions which are similar to those of a fluidized bed reactor Fischer-Tropsch process, for the purpose of selectively removing the reaction water from the reactor.

Two mordenite membranes (MOR1 and MOR2) were prepared by in-situ hydrothermal synthesis onto a commercially available α-alumina tubular support obtained from Societe des Ceramiques Techniques of France, following a procedure known to those skilled in the art, as described in M. A. Salomon, J. C. Coronas, M. Menéndes and J. Santamaria in: Chemical Communications (1998), pgs 125–126. About 80 mg of zeolite per alumina support was achieved at the end of the synthesis. Significant amounts of ZSM-5 and chabazite were also found to be present in the zeolite material, using x-ray diffraction ('XRD') analysis. Scanning Electron Microscopy ('SEM') analysis showed an approximately 10 μm thickness of the top layer; this indicates that about 85% of the zeolite material, after hydrothermal synthesis, was located inside the pores of the alumina support. The permeation areas obtained were 9.2 cm$^2$ for MOR1 and 8.8 cm$^2$ respectively.

Figure 3:
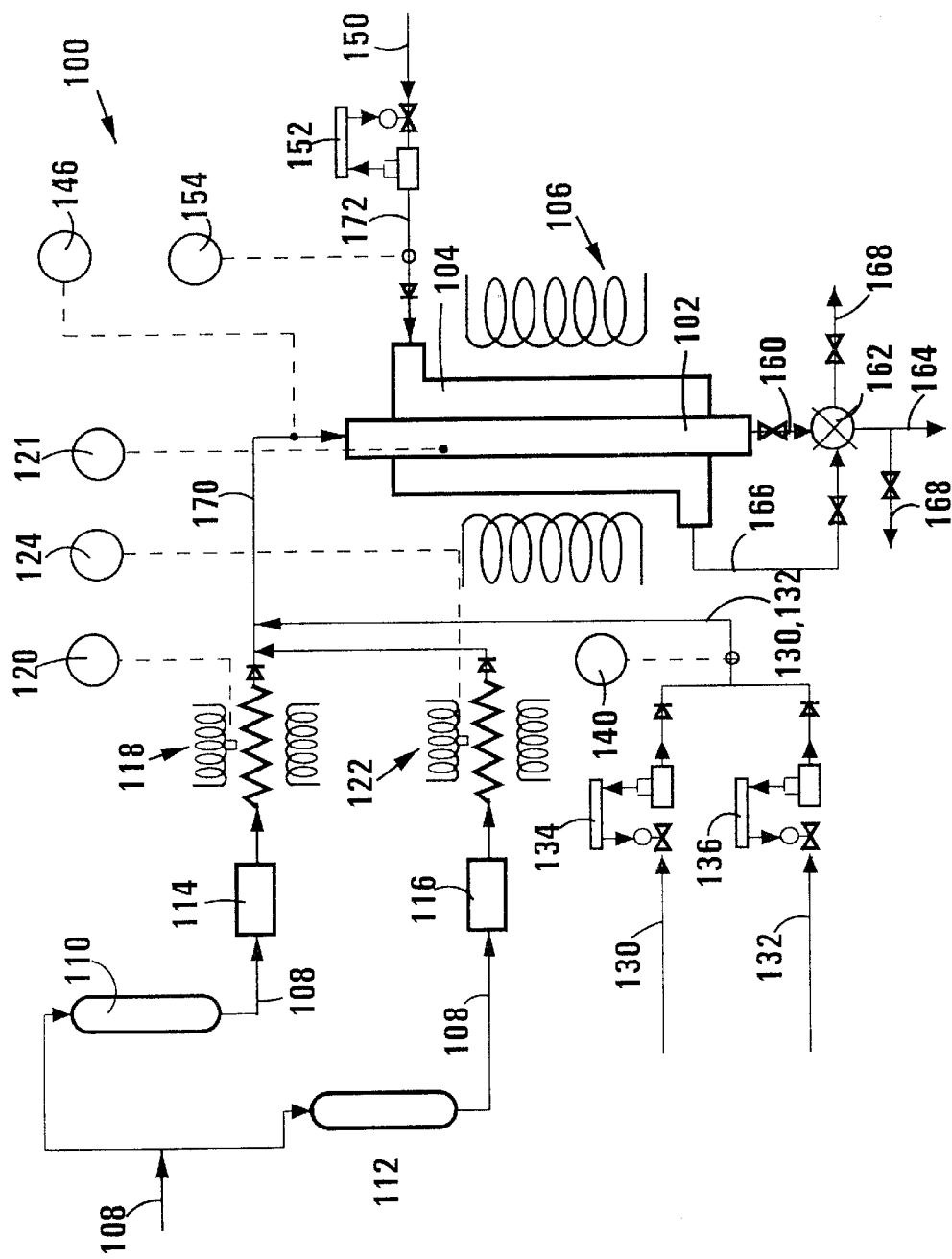
FIG. 3 shows, in simplified flow diagram form and on laboratory scale, apparatus for carrying out the process according to the invention for producing hydrocarbons.

An experimental laboratory scale apparatus or set-up to demonstrate the separation dynamics between the water and typical hydrocarbons and gases found inside a commercial Fischer-Tropsch reactor is indicated by reference numeral 100 in FIG. 3. Thus, FIG. 3 depicts laboratory scale apparatus for carrying out the process of the invention for producing hydrocarbons.

The set-up 100 includes a tubular water separation device 102 comprising the tubular α-alumina support and the mordenite membrane (MOR1 or MOR2) located against the outer surface of the support. The separation device 102 is located in a stainless steel module 104, with sealing of the separation device to the module being effected by means of silicone O-rings. The pressure inside the separation device 102 is measured by means of a pressure measurement device 146. The module 104 is located in an electrical furnace 106 controlled by a temperature control 121.

The set-up 100 also includes a nitrogen supply line 108, for supplying nitrogen at 30 bar. A branch of the supply line 108 leads through a deionized water supply 110, through a mass flow controller 114, through a preheater 118 controlled by a temperature control unit 120, and into a flow line 170 which leads into the upper end of the central passageway of the separation device 102. A branch of the nitrogen supply line 108 also leads through a n-octane supply 112, through a mass flow controller 116, through a preheater 122 controlled by temperature control unit 124, and into the flow line 170.

The set-up 100 also includes a supply line 130 for supplying a gaseous mixture of methane, carbon dioxide and hydrogen. The supply line 130 leads through a mass flow controller 134 and into the flow line 170. The set-up 100 further includes a supply line 132 for supplying a gaseous mixture of methane, carbon dioxide, carbon monoxide and hydrogen. The supply line 132 leads through a mass flow controller 136 and into the flow line 130. The pressure of the gaseous mixture in the flow line 130, 132 is measured by means of a pressure measurement device 140.

The set-up 100 also includes a nitrogen supply line 150 leading into a mass flow controller 152, with a flow line 172 leading from the controller 152 into the module 104. The pressure in the nitrogen supply line 150 is measured by means of the pressure measurement device 154. Thus, in use, nitrogen (or any other gas chosen) sweep gas passes along the outer tubular surface of the device 102 ie along the membrane, while the water and gaseous mixtures from the flow lines 130 or 132 pass along the inner tubular surface thereof.

A retentate withdrawal line or conduit 160 leads from the inside of the separation device 102 to a sample switching valve 162 and from there a line 164 leads to a gas chromatography analyzer (not shown).

A permeate withdrawal line 166 leads from the module 104, in proximity to the outlet end of the device 102, to the sample switching valve 162. Vent lines 168 are provided, with one of them leading from the line 164.

The aim of this example was to show the system ability to carry out separation of water (W) from other species, at conditions typical of a commercial fluidized Fischer-Tropsch reactor, ie temperature around 350° C. and a total pressure of 20–25 bar. The term 'other species' includes those likely to be present in a Fischer-Tropsch reactor: n-octane ($C_8$) as an example of hydrocarbons, $H_2$, $CH_4$, $CO_2$ and CO. These were fed as multicomponent mixtures to the membrane tube side. The separation device 102 was placed in the stainless steel module 104, which was sealed using graphite gaskets. To perform an experiment, a mass flow controlled stream (molar ratio $H_2/CH_4/CO_2$=44/44/12) was mixed with water and n-octane, which were fed initially as liquids by means of the two liquid mass flow controllers 114, 116 respectively, then passed through the evaporators 118, 122 respectively whose temperatures were fixed at 400° C. In some experiments, CO was added to the above described permanent gas mixture, in the proportions shown below. In addition, $N_2$ was used as a sweep gas on the retentate side, and therefore had to be taken into account when reporting the permeate side composition.

The mixed feedstream entered the tube side of the membrane module, while the shell side was swept with a flux of $N_2$. Concentrations of all of the above components in the retentate ($x_1$) and the permeate ($y_1$) were analyzed by gas chromatography using thermal conductivity ('TCD') and flame ionization ('FID') detectors. Several anlayses were carried out until approximately steady-state was reached in the permeate and retentate streams. This typically involved maintaining the system at operating conditions for 3 to 6 hours.

The flow rates of both the retentate and permeate streams ($F_{RM}$ and $F_{PM}$, respectively) were measured at room temperature and pressure by means of a bubble flowmeter, after condensation of water and n-octane. The total molar flow rates at the retentate and permeate sides ($F_R$ and $F_P$, respectively) can be calculated from these, taking into account the GC analysis of both streams and the saturation pressure of water and n-octane at the condensation temperature, in accordance with equations (3) to (6):

$$F_R = \frac{F_{RM}}{\sum x_i + (x_w + x_{C8})_{saturation}}, i \neq w, C_8 \qquad (3)$$

$$F_P = \frac{F_{PM}}{\sum y_i + (y_w + y_{C8})_{saturation}}, i \neq w, C_8 \qquad (4)$$

$$F_{Pi} = F_P \cdot x_i, i = W, C_8, H_2, CH_4, CO_2 \text{ and CO} \qquad (5)$$

$$F_{Ri} = F_R \cdot y_1, i = W, H_2, CH_4, CO_2 \text{ and CO} \qquad (6)$$

The feed flow rate for each component, $F_{Ei}$, was calculated as the addition of the molar flow rates thereof at the retentate and permeate sides, using equation (7). Permeances for each component ($Per_i$) were calculated using equation (8), where $\Delta P_1$ and $\Delta P_2$ are the driving forces (partial pressure difference between the retentate and permeate streams) for each component at the entrance and exit of the membrane module, respectively, and A the available permeation area.

The performance of the separation is customarily expressed in terms of separation selectivities: The water/species$_i$ selectivity ($S_{W/i}$), was calculated as the ratio of permeances using equation (9), while the separation factors $\alpha$ w/i were calculated as indicated in equation (10), ie as the quotient between the ratio of molar fractions of water and any species 'i' in the permeate and retentate sides. The advantage of using the separation factor is that it is obtained directly from GC analysis, and is not affected by errors in the overall mass balance.

$$F_{E1} = F_{R1} + F_{P1}, \; i = W, C_8, H_2, CH_4, CO_2 \text{ and } CO \quad (7)$$

$$Per_i = \frac{F_{Pi}}{\frac{(\Delta P_1 - \Delta P_2)_1}{\ln\left(\frac{\Delta P_1}{\Delta P_2}\right)_i} \cdot A}, \; 1 = W, \quad (8)$$

$C8, H2, CH4, CO2$ and $CO$ $$S_{W/i} = \frac{Per_w}{Per_i}, \; i \neq w \quad (9)$$

$$\alpha_{W/i} = \frac{y_w / y_i}{x_w / x_i}, \; i \neq w \quad (10)$$

The conditions for the different experiments (pressure on both membrane sides, temperature, calculated molar feed rates for each component), and the results obtained (molar feed rates for each component in the permeate, water permeation flux, separation factors and separation selectivities) for the MOR1 and MOR2 membranes are given in Table 1.

reactor, that is, to separate the water from hydrocarbons, carbon monoxide, carbon dioxide and hydrogen.

In this Example, the water flux tends to increase with the partial pressure of water in the feed, while the separation selectivities and separation factors tend to increase with the flow of the sweep gas, which is in this case nitrogen.

EXAMPLE 2

In this example, the same set-up 100 as used in Example 1, was used; however, a different tubular separation device 102 to that described in Example 1 was used.

In this case, two similar ZSM-5 membranes, ZSM5P1 and ZSM5P2 were deposited on the outer surfaces of porous stainless steel tubular supports following a procedure known to those skilled in the art, as described by J. Coronas, J. L. Falconer and R. D. Noble in Preparation, characterization and permeation properties of tubular ZSM-5 composite membranes, AlChE J., 43(7) (1997) pages 1797–1812. The permeation area for both membranes was similar, at 8 cm$^2$ each.

The use of porous stainless steel supports facilitates the industrial application of this invention because of their superior mechanical strength, as compared to the alpha-alumina tubular supports used in Example 1.

The experimental procedure and data analysis were similar to those described in Example 1. The results obtained are shown in Table 2 for the membrane ZSM5P1 and in Table 3 for the membrane ZSM5P2.

Tables 2 and 3 clearly show that the ZSM-5 membranes, deposited on a porous stainless steel support, are able to selectively separate water from hydrocarbons, carbon monoxide, carbon dioxide and hydrogen, at conditions similar to those found in commercial fluidized Fischer-Tropsch reactors.

In this Example, the water flux also showed a tendency to increase with the partial pressure of water in the feed while

TABLE 1

Mordenite membranes on alumina supports MOR1 (Experiments 1 and 2) and MOR2 (Experiments 3 and 4)

| | | | | Feed | | | | | | | | Permeate | | | | | |
|---|---|---|---|---|---|---|---|---|---|---|---|---|---|---|---|---|---|
| | Temp | $P_T$ | $P_W$ | Component Flow (mmol/min) | | | | | | $P_T$ | | Component Flow (mmol/min) | | | | | |
| Run | (° C.) | (bar) | (bar) | W | $C_8$ | $H_2$ | $CH_4$ | $CO_2$ | CO | (bar) | $N_2$ | W | $C_8$ | $H_2$ | $CH_4$ | $CO_2$ | CO |
| 1 | 355 | 19.7 | 7.90 | 16.7 | 3.39 | 12.7 | 13.2 | 2.58 | — | 18.6 | 14.8 | 9.71 | 0.55 | 3.69 | 3.58 | 0.64 | — |
| 2 | 349 | 22.3 | 6.85 | 12.5 | 3.31 | 10.8 | 12.1 | 2.01 | — | 21.2 | 15.4 | 6.87 | 0.68 | 3.20 | 3.60 | 0.54 | — |
| 3 | 349 | 19.8 | 8.25 | 23.5 | 2.86 | 13.2 | 14.4 | 2.33 | — | 18.6 | 9.56 | 13.5 | 0.77 | 6.40 | 5.90 | 0.90 | — |
| 4 | 350 | 22.4 | 9.43 | 25.2 | 2.32 | 14.6 | 15.2 | 2.49 | 3.23 | 20.7 | 9.20 | 16.9 | 1.43 | 10.1 | 10.1 | 1.57 | 2.21 |

| | Water flux | Separation Selectivity | | | | | Separation Factor | | | | |
|---|---|---|---|---|---|---|---|---|---|---|---|
| Run | (kg · m$^{-2}$ · h$^{-1}$) | W/$C_8$ | W/$H_2$ | W/$CH_4$ | W/$CO_2$ | W/CO | W/$C_8$ | W/$H_2$ | W/$CH_4$ | W/$CO_2$ | W/CO |
| 1 | 12.8 | 9.7 | 4.5 | 5.4 | 10 | — | 3.7 | 2.0 | 2.3 | 3.8 | — |
| 2 | 9.09 | 8.6 | 5.2 | 5.1 | 5.9 | — | 4.7 | 2.9 | 3.8 | 3.3 | — |
| 3 | 17.9 | 7.1 | 2.4 | 3.5 | 3.9 | — | 3.7 | 1.4 | 1.9 | 2.2 | — |
| 4 | 22.4 | 1.4 | 0.8 | 1.0 | 1.3 | 3.7 | 1.3 | 0.9 | 1.0 | 1.2 | 3.0 |

Table 1 clearly shows that at temperatures and pressures typical of those expected in a commercial fluidized bed reactor, the zeolite membrane is able to selectively separate the water from the other species found in such commercial the separation selectivities and separation factors showed a tendency to increase with the flow of the sweep gas (in this case nitrogen), or more accurately, with the partial pressure of the sweep gas in the permeate.

TABLE 2

ZSM-5 membrane on stainless steel support-ZSM5P1

| | | | | Feed | | | | | | | | Permeate | | | | | |
|---|---|---|---|---|---|---|---|---|---|---|---|---|---|---|---|---|---|
| | Temp | $P_T$ | $P_W$ | | Component Flow (mmol/min) | | | | | $P_T$ | | Component Flow (mmol/min) | | | | | |
| Run | (°C.) | (bar) | (bar) | W | $C_8$ | $H_2$ | $CH_4$ | $CO_2$ | CO | (bar) | $N_2$ | W | $C_8$ | $H_2$ | $CH_4$ | $CO_2$ | CO |
| 5 | 353 | 18.7 | 7.3 | 21 | 1.8 | 13.4 | 14.5 | 2.5 | — | 18.5 | 10.0 | 7.8 | 0.1 | 3.2 | 1.4 | 0.4 | — |
| 6 | 367 | 20.0 | 7.5 | 18.4 | 1.5 | 12.4 | 14.3 | 2.4 | — | 18.7 | 13.8 | 5.1 | 0.1 | 2.2 | 1.2 | 0.2 | — |
| 7 | 298 | 22.3 | 8.3 | 22.5 | 2.8 | 13.7 | 13.7 | 3.0 | — | 1.8 | 12.1 | 6.0 | 0.1 | 1.2 | 0.6 | 0.2 | — |
| 8 | 356 | 17 | 8.9 | 29.0 | 3.7 | 15.4 | 14.9 | 3.3 | — | 15.9 | 10.0 | 10.0 | 0.3 | 3.0 | 1.5 | 0.6 | — |
| 9 | 348 | 19.2 | 2.3 | 6.29 | 1.4 | 16.4 | 13.8 | 4.18 | — | 17.4 | 9.3 | 2.4 | 0.2 | 3.4 | 1.7 | 0.7 | — |
| 10 | 352 | 21.0 | 2.2 | 6.8 | 1.9 | 14.6 | 13.4 | 4.2 | — | 19.5 | 25.1 | 1.9 | 0.06 | 0.8 | 0.2 | 0.3 | — |
| 11 | 346 | 20.6 | 2.2 | 7.5 | 2.0 | 15.8 | 15.3 | 4.3 | — | 19.4 | 24.8 | 1.7 | 0.04 | 0.7 | 0.2 | 0.4 | — |
| 12 | 353 | 18.3 | 2.1 | 10.0 | 0.7 | 22.4 | 18.1 | 7.8 | — | 17.8 | 24.6 | 2.5 | 0.02 | 1.2 | 0.4 | 0.7 | — |
| 13 | 345 | 20.1 | 1.9 | 13.9 | 1.2 | 47.4 | 37.0 | 16.1 | — | 18.2 | 26.7 | 2.3 | 0.02 | 1.6 | 0.6 | 0.7 | — |
| 14 | 343 | 18.8 | 2.1 | 22.9 | 1.2 | 71.5 | 55.0 | 20.7 | — | 18.3 | 27.2 | 2.4 | 0.01 | 1.4 | 0.5 | 0.5 | — |
| 15 | 350 | 18.0 | 2.8 | 15.3 | 0.9 | 24.7 | 15.7 | 5.8 | 8.8 | 16.5 | 24.9 | 3.1 | 0.2 | 1.8 | 0.7 | 0.1 | 0.4 |
| 16 | 346 | 18.5 | 3.0 | 16.6 | 1.3 | 26.8 | 17.3 | 4.6 | 11.8 | 16.8 | 23.6 | 3.0 | 0.3 | 1.8 | 0.7 | 0.2 | 0.6 |

| | Water flux | | Separation Selectivity | | | | | Separation Factor | | | |
|---|---|---|---|---|---|---|---|---|---|---|---|
| Run | (kg · m$^{-2}$ · h$^{-1}$) | W/$C_8$ | W/$H_2$ | W/$CH_4$ | W/$CO_2$ | W/CO | W/$C_8$ | W/$H_2$ | W/$CH_4$ | W/$CO_2$ | W/CO |
| 5 | 8.3 | 8.7 | 2.2 | 6.9 | 3.8 | — | 6.8 | 1.8 | 5.4 | 3.0 | — |
| 6 | 5.4 | 4.1 | 1.9 | 4.3 | 3.7 | — | 3.7 | 1.8 | 3.9 | 3.4 | — |
| 7 | 8.4 | 5.5 | 2.1 | 4.1 | 4.5 | — | 4.6 | 1.8 | 3.5 | 3.8 | — |
| 8 | 10.6 | 16.4 | 5.8 | 13.6 | 6.8 | — | 5.5 | 2.2 | 4.6 | 2.5 | — |
| 9 | 3.34 | 15.4 | 2.4 | 14.9 | 9.9 | — | 4.7 | 2.4 | 4.5 | 3.1 | — |
| 10 | 2.65 | 14.2 | 7.7 | 24.3 | 4.6 | — | 12.4 | 6.8 | 21.3 | 4.1 | — |
| 11 | 2.29 | 16.3 | 6.7 | 27.1 | 2.7 | — | 14.5 | 6.0 | 24.1 | 2.5 | — |
| 12 | 3.43 | 15.2 | 7.3 | 18.4 | 3.9 | — | 12.2 | 5.9 | 14.7 | 3.2 | — |
| 13 | 3.07 | 12.7 | 7.0 | 14.4 | 4.8 | — | 9.8 | 5.5 | 11.1 | 3.8 | — |
| 14 | 3.28 | 20.0 | 7.7 | 16.5 | 5.1 | — | 14.9 | 5.9 | 12.4 | 4.0 | — |
| 15 | 4.22 | 11.7 | 3.8 | 6.3 | 10.6 | 5.8 | 9.8 | 3.3 | 5.4 | 8.9 | 4.9 |
| 16 | 4.05 | 9.8 | 3.4 | 5.3 | 5.3 | 4.9 | 8.5 | 3.0 | 4.6 | 4.6 | 4.3 |

TABLE 3

ZSM-5 membrane on stainless steel support-ZSM5P2

| | | | | Feed | | | | | | | | Permeate | | | | | |
|---|---|---|---|---|---|---|---|---|---|---|---|---|---|---|---|---|---|
| | Temp | $P_T$ | $P_W$ | | Component Flow (mmol/min) | | | | | $P_T$ | | Component Flow (mmol/min) | | | | | |
| Run | (°C.) | (bar) | (bar) | W | $C_8$ | $H_2$ | $CH_4$ | $CO_2$ | CO | (bar) | $N_2$ | W | $C_8$ | $H_2$ | $CH_4$ | $CO_2$ | CO |
| 17 | 357 | 19.0 | 1.8 | 3.5 | 1.3 | 14.9 | 11.5 | 3.9 | — | 18.1 | 12.7 | 1.3 | 0.1 | 1.8 | 1.3 | 0.2 | — |
| 18 | 357 | 19.7 | 2.0 | 3.8 | 1.4 | 15.4 | 11.6 | 4.3 | — | 18.5 | 12.0 | 1.4 | 0.1 | 2.1 | 1.1 | 0.4 | — |
| 19 | 355 | 21.6 | 2.8 | 5.6 | 1.7 | 17.3 | 13.4 | 4.7 | — | 20.7 | 25.3 | 2.6 | 0.2 | 2.2 | 1.2 | 0.4 | — |
| 20 | 355 | 21.1 | 3.8 | 12.2 | 1.8 | 22.4 | 15.8 | 4.4 | 11.3 | 19.9 | 25.9 | 3.3 | 0.1 | 1.6 | 0.8 | 0.2 | 0.4 |
| 21 | 359 | 18.5 | 2.5 | 8.5 | 1.7 | 20.4 | 14.9 | 5.2 | 10.9 | 16.5 | 25.6 | 3.3 | 0.1 | 1.6 | 0.7 | 0.2 | 0.6 |
| 22 | 357 | 16.0 | 2.2 | 5.2 | 1.2 | 14.9 | 11.3 | 4.2 | — | 15.2 | 23.4 | 2.3 | 0.1 | 1.4 | 0.7 | 0.2 | — |
| 23 | 347 | 16.3 | 3.1 | 7.9 | 1.2 | 15.8 | 12.3 | 4.2 | — | 15.3 | 48.1 | 4.9 | 0.09 | 1.4 | 0.8 | 0.2 | — |
| 24 | 342 | 16.7 | 2.8 | 7.1 | 2.7 | 15.6 | 12.3 | 4.2 | — | 15.4 | 35.5 | 4.0 | 0.1 | 1.6 | 0.9 | 0.3 | — |
| 25 | 342 | 18.1 | 3.3 | 7.2 | 1.6 | 14.8 | 11.7 | 4.1 | — | 17.2 | 58.0 | 4.8 | 0.1 | 1.4 | 0.6 | 0.2 | — |

| | Water flux | | Separation Selectivity | | | | | Separation Factor | | | |
|---|---|---|---|---|---|---|---|---|---|---|---|
| Run | (kg · m$^{-2}$ · h$^{-1}$) | W/$C_8$ | W/$H_2$ | W/$CH_4$ | W/$CO_2$ | W/CO | W/$C_8$ | W/$H_2$ | W/$CH_4$ | W/$CO_2$ | W/CO |
| 17 | 1.83 | 14.9 | 10.3 | 15.9 | 20.5 | — | 6.4 | 4.5 | 6.8 | 8.8 | — |
| 18 | 1.98 | 12.8 | 8.4 | 13.8 | 14.0 | — | 5.8 | 3.9 | 6.2 | 6.3 | — |
| 19 | 3.50 | 11.0 | 8.4 | 12.6 | 14.8 | — | 7.5 | 5.8 | 8.6 | 10.0 | — |
| 20 | 4.46 | 7.6 | 5.9 | 7.7 | 10.7 | 13.2 | 6.0 | 4.7 | 6.0 | 8.4 | 10.3 |
| 21 | 4.47 | 12.9 | 13.2 | 23.5 | 24.6 | 18.8 | 7.3 | 7.4 | 13.0 | 13.6 | 10.5 |
| 22 | 3.13 | 11.9 | 10.1 | 17.3 | 19.5 | — | 8.9 | 7.5 | 12.8 | 14.6 | — |
| 23 | 6.68 | 24.9 | 20.3 | 27.3 | 40.5 | — | 20.2 | 16.4 | 22.1 | 33.0 | — |
| 24 | 5.43 | 27.4 | 15.4 | 21.7 | 24.7 | — | 19.4 | 10.8 | 15.4 | 17.5 | — |
| 25 | 6.50 | 25.1 | 21.0 | 38.8 | 34.2 | — | 22.8 | 18.9 | 35.4 | 31.2 | — |

EXAMPLE 3

In this Example, the same ZSM5P2 membrane used in Example 2 was used, but the temperature range was expanded to include lower temperatures.

The experimental results obtained are shown in Table 4. From Table 4, it is clear that the zeolite membrane, deposited on a porous stainless steel support, is able to selectively separate water from hydrocarbons, carbon monoxide, carbon dioxide and hydrogen, at temperatures as low as 150° C.

The separation factors and separation selectivities shown in Table 4 are higher at the lower temperatures (eg 150° C. and 196° C.), while there is not much difference in the separation selectivities and separation factors in the temperature range of about 241° C. to about 359° C. (Tables 3 and 4) at similar sweep gas (in this example nitrogen) flow rates or, more accurately, at similar partial pressures of the sweep gas in the retentate.

This shows that the zeolite membranes are able to separate water from hydrocarbons, carbon monoxide, carbon dioxide and hydrogen at temperatures typical of slurry bed Fischer-Tropsch commercial reactors operating with either cobalt or iron based catalysts, ie at about 190° C. to 260° C., as well as at temperatures typical of fluidized Fischer-Tropsch commercial reactors operating with iron based catalysts, ie at about 320° C. to 360° C.

the catalyst particles, as would be the case if the separation devices of Examples 1 to 3 were located directly in a fluidized bed so that the membrane would be in direct contact with the fluidized bed; this is in order to avoid possible attrition of the zeolite membrane caused by its contact with the fluidized catalyst particles.

It may therefore be preferable that the zeolite membrane is deposited on the opposite side of the porous support to that which would be in contact with the catalyst particles. This can be achieved, in practice, by depositing a zeolite membrane on the internal surface of a porous stainless steel support and introducing the sweep gas into the tube side of the membrane. Therefore, the effect of feeding the sweep gas through the tube side of the membrane, while passing the water and the mixtures of hydrocarbons, carbon dioxide, carbon monoxide and hydrogen along the shell side of the tubular membrane was investigated.

The experiments took place in the same set-up 100, by swopping the entry positions of the flow lines 170 and 172 into the separation device 102 and module 104.

The results obtained at various temperatures are shown in Table 5. This table shows clearly that the zeolite membrane is able to selectively separate water from hydrocarbons, carbon monoxide, carbon dioxide and hydrogen, when the sweep gas is fed internally into the tubular membrane and the water, hydrocarbons, carbon monoxide, carbon dioxide

TABLE 4

ZSM-5 membrane on stainless steel support-ZSM5P2

| | | | | Feed | | | | | | | | Permeate | | | | | |
|---|---|---|---|---|---|---|---|---|---|---|---|---|---|---|---|---|---|
| | Temp | $P_T$ | $P_W$ | Component Flow (mmol/min) | | | | | | $P_T$ | | Component Flow (mmol/min) | | | | | |
| Run | (° C.) | (bar) | (bar) | W | $C_8$ | $H_2$ | $CH_4$ | $CO_2$ | CO | (bar) | $N_2$ | W | $C_8$ | $H_2$ | $CH_4$ | $CO_2$ | CO |
| 26 | 150 | 20.9 | 3.84 | 6.9 | 0.6 | 13 | 11 | 6.5 | — | 20.0 | 47 | 4.7 | 0.02 | 0.4 | 0.3 | 0.6 | — |
| 27 | 196 | 19.5 | 3.34 | 7.4 | 0.7 | 14 | 13 | 7.6 | — | 18.7 | 45 | 4.3 | 0.02 | 0.3 | 0.5 | 0.1 | — |
| 28 | 241 | 17.7 | 2.02 | 10 | 0.5 | 30 | 24 | 5.5 | — | 16.9 | 47 | 3.9 | 0.03 | 0.8 | 0.7 | 0.9 | — |
| 29 | 241 | 18.8 | 2.16 | 7.4 | 0.5 | 25 | 19 | 12 | — | 17.5 | 44 | 3.7 | 0.03 | 1.3 | 1.1 | 1.6 | — |
| 30 | 249 | 18.8 | 3.77 | 11 | 1.5 | 19 | 19 | 6.5 | — | 17.7 | 46 | 6.2 | 0.06 | 1.0 | 0.8 | 0.6 | — |
| 31 | 244 | 18.8 | 3.81 | 12 | 0.7 | 22 | 18 | 7.7 | — | 18.3 | 46 | 6.0 | 0.03 | 0.8 | 0.7 | 0.7 | — |
| 32 | 347 | 16.3 | 3.10 | 7.9 | 1.2 | 16 | 12 | 4.2 | — | 15.3 | 48 | 4.9 | 0.09 | 1.4 | 0.8 | 0.2 | — |
| 33 | 246 | 21.2 | 2.08 | 8.2 | 1.0 | 15 | 13 | 5.3 | — | 20.5 | 24 | 3.1 | 0.06 | 0.6 | 0.5 | 0.6 | — |
| 34 | 245 | 20.7 | 4.78 | 9.5 | 1.3 | 13 | 13 | 4.2 | — | 19.6 | 35 | 5.8 | 0.10 | 1.0 | 0.8 | 0.9 | — |
| 35 | 246 | 21.0 | 5.06 | 11 | 1.5 | 14 | 12 | 6.2 | — | 20.3 | 55 | 6.1 | 0.07 | 0.6 | 0.5 | 1.1 | — |
| 36 | 242 | 19.2 | 2.93 | 10 | 0.9 | 22 | 20 | 10 | 3.4 | 18.5 | 45 | 4.6 | 0.03 | 0.5 | 0.9 | 0.8 | 0.2 |
| 37 | 246 | 20.6 | 3.14 | 6.7 | 0.6 | 14 | 12 | 7.0 | 4.0 | 19.3 | 45 | 5.0 | 0.04 | 0.6 | 0.7 | 1.3 | 0.3 |

| | Water flux | Separation Selectivity | | | | | Separation Factor | | | | |
|---|---|---|---|---|---|---|---|---|---|---|---|
| Run | (kg · m$^{-2}$ · h$^{-1}$) | W/C$_8$ | W/H$_2$ | W/CH$_4$ | W/CO$_2$ | W/CO | W/C$_8$ | W/H$_2$ | W/CH$_4$ | W/CO$_2$ | W/CO |
| 26 | 6.40 | 80.0 | 76.0 | 72.1 | 58.3 | — | 69.5 | 72.9 | 66.0 | 21 | — |
| 27 | 5.9 | 62.6 | 65.6 | 44.5 | 10.7 | — | 51.7 | 54.1 | 36.6 | 8.7 | — |
| 28 | 5.32 | 19.6 | 25.3 | 23.0 | 3.6 | — | 17.1 | 22.1 | 20.1 | 3.0 | — |
| 29 | 5.02 | 22.6 | 27.6 | 23.9 | 9.5 | — | 15.5 | 18.8 | 16.4 | 6.5 | — |
| 30 | 8.38 | 33.9 | 29.2 | 35.2 | 16.2 | — | 23.9 | 20.6 | 24.9 | 11 | — |
| 31 | 8.17 | 30.9 | 30.7 | 30.9 | 11.9 | — | 23.9 | 23.8 | 24.0 | 9.3 | — |
| 32 | 6.68 | 24.9 | 20.3 | 27.3 | 40.5 | — | 20.2 | 16.4 | 22.1 | 33.0 | — |
| 33 | 4.26 | 12.6 | 18.9 | 18.4 | 5.9 | — | 9.8 | 14.6 | 14.2 | 4.7 | — |
| 34 | 7.89 | 43.2 | 49.0 | 57.4 | 13.8 | — | 16.6 | 18.8 | 22.0 | 5.2 | — |
| 35 | 8.27 | 25.1 | 27.5 | 30.4 | 5.6 | — | 25.1 | 27.5 | 30.4 | 5.5 | — |
| 36 | 6.26 | 36.6 | 49.7 | 22.0 | 12.4 | 19.6 | 26.7 | 36.2 | 16.1 | 9.1 | 14.3 |
| 37 | 6.78 | 23.2 | 36.0 | 26.8 | 7.4 | 18.8 | 18.8 | 29.2 | 21.7 | 5.9 | 15.2 |

EXAMPLE 4

For an industrial application of this invention, it may be preferable for the zeolite membrane not to be in contact with and hydrogen are fed to the shell side of the tubular membrane, therefore simulating more closely a possible industrial application of this invention.

TABLE 5

ZSM-5 membrane on stainless steel support-Exterior feed - ZSM5P2

| | | | Feed | | | | | | | Permeate | | | | | | |
|---|---|---|---|---|---|---|---|---|---|---|---|---|---|---|---|---|
| | Temp | $P_T$ | $P_W$ | Component Flow (mmol/min) | | | | | | $P_T$ | Component Flow (mmol/min) | | | | | |
| Run | (° C.) | (bar) | (bar) | W | $C_8$ | $H_2$ | $CH_4$ | $CO_2$ | CO | (bar) | $N_2$ | W | $C_8$ | $H_2$ | $CH_4$ | $CO_2$ | CO |
| 38 | 244 | 17.2 | 7.93 | 24 | 0.5 | 14 | 9.3 | 4.9 | — | 16.6 | 45 | 14 | 0.03 | 0.4 | 0.3 | 0.5 | — |
| 39 | 240 | 20.4 | 4.86 | 18 | 0.5 | 30 | 18 | 9.4 | — | 19.7 | 45 | 8.6 | 0.01 | 0.6 | 0.4 | 0.6 | — |
| 40 | 243 | 19.8 | 3.10 | 16 | 0.4 | 47 | 24 | 16 | — | 18.6 | 43 | 6.4 | 0.01 | 0.7 | 0.7 | 0.4 | — |
| 41 | 359 | 20.8 | 4.43 | 17 | 0.4 | 32 | 18 | 12 | — | 19.7 | 45 | 8.6 | 0.03 | 2.9 | 1.2 | 0.6 | — |

| | Water flux | Separation Selectivity | | | | | Separation Factor | | | | |
|---|---|---|---|---|---|---|---|---|---|---|---|
| Run | (kg · m$^{-2}$ · h$^{-1}$) | W/$C_8$ | W/$H_2$ | W/$CH_4$ | W/$CO_2$ | W/CO | W/$C_8$ | W/$H_2$ | W/$CH_4$ | W/$CO_2$ | W/CO |
| 38 | 19.48 | 25.4 | 48.4 | 41.5 | 13.8 | — | 22.4 | 42.9 | 36.7 | 12.1 | — |
| 39 | 11.7 | 50.3 | 79.0 | 58.8 | 24.0 | — | 28.5 | 44.6 | 33.3 | 13.6 | — |
| 40 | 8.72 | 50.6 | 80.1 | 47.3 | 53.4 | — | 20.9 | 43.0 | 22.0 | 22.1 | — |
| 41 | 11.7 | 23.5 | 18.3 | 25.6 | 36.6 | — | 13.0 | 10.2 | 14.1 | 20.3 | — |

EXAMPLE 5

This example illustrates the suitability of zeolite membranes for the separation of water from hydrocarbons, carbon monoxide, carbon dioxide and hydrogen in a slurry bed reactor.

Figure 4:
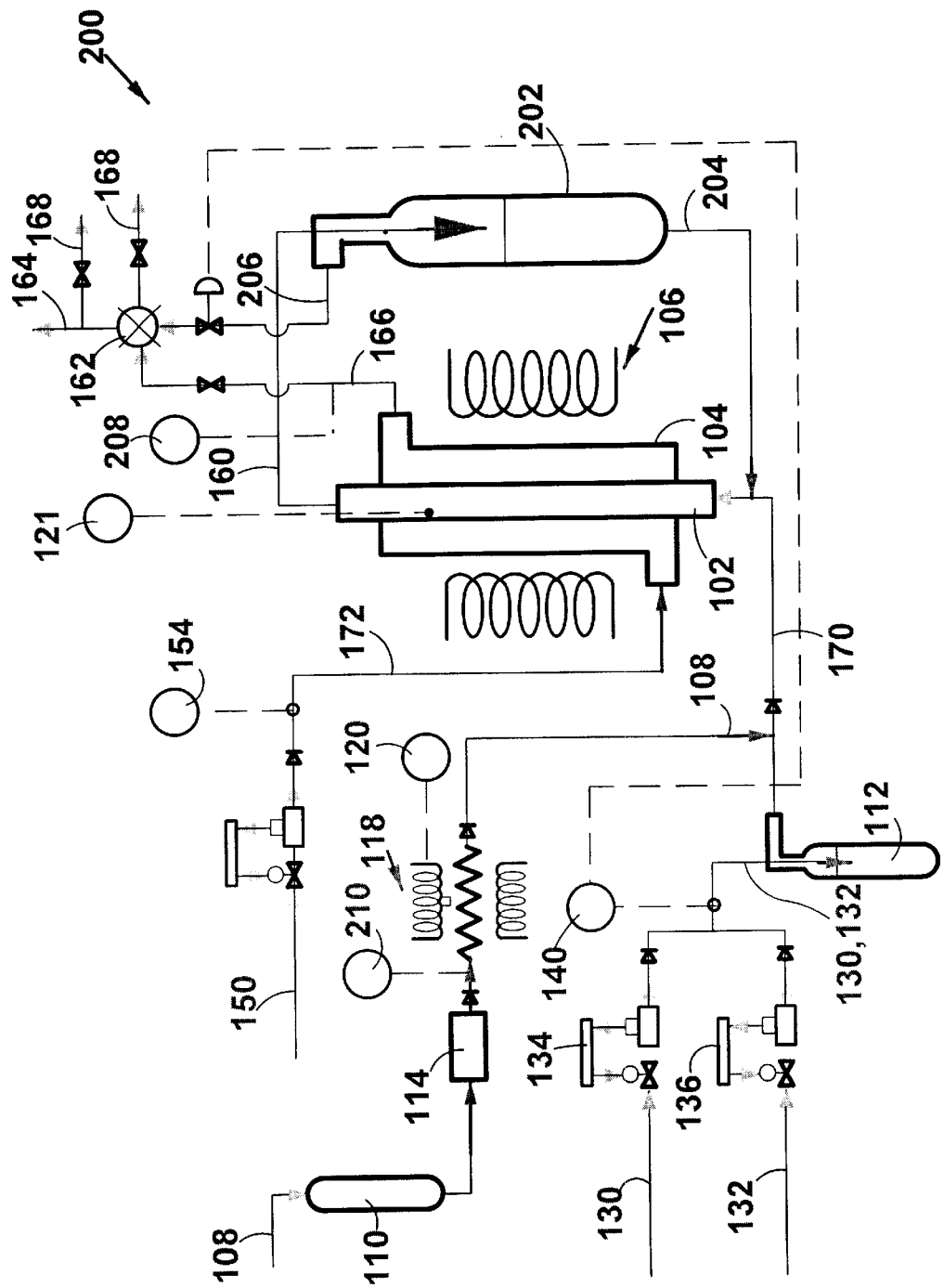
FIG. 4 shows, in simplified flow diagram form and on laboratory scale, apparatus similar to that of FIG. 3, for carrying out the process according to the invention for producing hydrocarbons.

The modifications that had to be performed on the experimental set-up 100 of FIG. 3, in order to simulate a slurry bed reactor, are shown in FIG. 4, in which the set-up is indicated by reference numeral 200. Parts of the set-up 200 which are the same or similar to those of the set-up 100, are indicated with the same reference numerals.

The feed line 170 is, in FIG. 4, connected to the bottom end of the tubular separation device 102, while the feed line 172 is connected to the bottom end of the stainless steel module 104. The permeate line 166 is connected to the upper end of the stainless steel module 104 while the retentate line 160 is connected to the upper end of the tubular separation device 102.

The n-octane supply 112 is linked (i) to the gaseous mixture flow line 130, with the gaseous mixture therein consisting of propane, methane, carbon dioxide and hydrogen, and (ii) to the gaseous supply line 132, which now feeds pure carbon monoxide. The purpose is to saturate the gaseous components in lines 130 and 132 with n-octane. The system 200 includes a vessel 202 containing n-octane. The inside of the tubular separation device 102 is now filled with n-octane by means of a line 204. The n-octane simulates the liquid hydrocarbons present in a commercial Fischer-Tropsch slurry bed reactor operating with either iron or cobalt based catalysts, and its level inside the tubular zeolite membrane 102 is controlled by means of the retentate line 160, which enters the vessel 202, therefore equalizing the pressure between the vessel 202 and the inside of the separation device 102.

A line 206 connects the retentate coming from the inside of the tubular separation device 102 via the vessel 202 to the sample switching valve 162. The pressure in the permeate line 166 is measured with a pressure measurement device 208, while the pressure of the sweep gas supply 108 is measured with a pressure measuring device 210.

The following zeolite membranes were tested in the set-up 200:

The ZSM-5 zeolite membrane ZSM5P2 described in Example 2

A silicalite membrane SIL2 deposited on the outer surface of a porous stainless steel tubular support following a procedure known to those skilled in the art, as described in MD. Jia, B. Chen, R. D. Noble and J. L. Falconer, J. Membrane Sci, 90 (1994) page 1

A mordenite/ZSM-5/chabazite membrane MORP2 prepared similarly to that described in Example 1, but using a porous stainless steel support, ie the membrane is also located on the outer surface of the support.

The results obtained using the membranes described above are shown in Tables 6 (ZSM5P2 membrane), 7 (SIL2 membrane) and 8 (MORP2 membrane). Tables 6 to 8 clearly demonstrate that these zeolite membranes are able to selectively remove water from a hydrocarbon in the liquid phase, saturated and containing bubbles of carbon monoxide, carbon dioxide, hydrogen, methane and gaseous hydrocarbons such as propane, at temperatures typical of those expected in a commercial slurry bed Fischer-Tropsch reactor operating with either iron or cobalt based catalysts.

TABLE 6

Membrane on stainless steel support; Slurry experiments - ZSM5P2

| | | | | Feed | | | | | | Permeate | | | | | | |
|---|---|---|---|---|---|---|---|---|---|---|---|---|---|---|---|---|
| | Temp | $P_T$ | $P_W$ | Component Flow (mmol/min) | | | | | $P_T$ | Component Flow (mmol/min) | | | | | | |
| Run | (° C.) | (bar) | (bar) | W | $H_2$ | $CH_4$ | $CO_2$ | | (bar) | $N_2$ | W | $C_8$ | $H_2$ | $CH_4$ | $CO_2$ | CO |
| 42 | 250 | 18.2 | 3.6 | 7.5 | 12.0 | 13.0 | 5.4 | | 17.5 | 50.4 | 3.6 | 0.3 | 2.3 | 1.8 | 0.5 | — |
| 43 | 248 | 21.5 | 4.0 | 7.0 | 11.9 | 12.8 | 5.7 | | 20.8 | 45.7 | 4.5 | 0.3 | 0.7 | 2.0 | 0.2 | |

TABLE 6-continued

Membrane on stainless steel support; Slurry experiments - ZSM5P2

| | Water Flow | $C_8$ Flow | Separation Factors | | |
|---|---|---|---|---|---|
| Run | (kg · m$^{-2}$ · h$^{-1}$) | (kg · m$^{-2}$ · h$^{-1}$) | W/H$_2$ | W/CH$_4$ | W/CO$_2$ |
| 42 | 4.9 | 2.6 | 36 | 43 | 35 |
| 43 | 6.1 | 2.4 | 25 | 8.9 | 16 |

TABLE 7

Silicalite membrane on stainless steel support; Slurry experiments - SIL2

| | | | | Feed | | | | | | | Permeate Component Flow (mmol/min) | | | | | | | |
|---|---|---|---|---|---|---|---|---|---|---|---|---|---|---|---|---|---|---|
| | Temp | $P_T$ | $P_W$ | Component Flow (mmol/min) | | | | | | $P_T$ | | | | | | | | |
| Run | (° C.) | (bar) | (bar) | W | H$_2$ | CH$_4$ | C$_3$ | CO | CO$_2$ | (bar) | N$_2$ | W | C$_8$ | H$_2$ | CH$_4$ | C$_3$ | CO | CO$_2$ |
| 44 | 248 | 20.5 | 0.34 | 0.4 | 18.3 | 4.5 | 3.2 | — | 0.4 | 18.8 | 45.7 | 0.1 | 0.6 | 0.4 | 0.02 | 0.4 | — | 0.02 |
| 45 | 254 | 21.8 | 0.33 | 0.6 | 22.5 | 5.4 | 3.8 | — | 0.4 | 19.2 | 37.3 | 0.5 | 0.2 | 6.8 | 1.7 | 1.2 | — | 1.10 |
| 46 | 257 | 22.3 | 1.13 | 2.0 | 24.6 | 4.1 | 4.3 | — | 0.3 | 20.2 | 41.9 | 1.5 | 0.2 | 4.0 | 0.5 | 0.8 | — | 0.02 |
| 47 | 253 | 22.1 | 0.98 | 1.8 | 22.5 | 5.0 | 3.8 | 6.0 | 0.4 | 19.7 | 50.0 | 1.6 | 0.3 | 8.1 | 0.7 | 2.9 | 2.4 | 0.09 |

| | Water Flow | $C_8$ Flow | Separation Factors | | | | |
|---|---|---|---|---|---|---|---|
| Run | (kg · m$^{-2}$ · h$^{-1}$) | (kg · m$^{-2}$ · h$^{-1}$) | W/H$_2$ | W/CH$_4$ | W/C$_3$ | W/CO | W/CO$_2$ |
| 44 | 0.2 | 5.8 | 23 | 127 | 3.2 | — | 9.5 |
| 45 | 0.7 | 1.8 | 28 | 25 | 26 | — | 24 |
| 46 | 2.0 | 2.1 | 13.6 | 67 | 11 | — | 42 |
| 47 | 2.2 | 2.5 | 22 | 72 | 22 | 4.8 | 44 |

TABLE 8

Mordenite/ZSM-5/chabazite membrane on stainless steel support; Slurry experiments - MORP2

| | | | | Feed | | | | | | Permeate | | | | | | |
|---|---|---|---|---|---|---|---|---|---|---|---|---|---|---|---|---|
| | Temp | $P_T$ | $P_W$ | Component Flow (mmol/min) | | | | | $P_T$ | Component Flow (mmol/min) | | | | | | |
| Run | (° C.) | (bar) | (bar) | W | H$_2$ | CH$_4$ | C$_3$ | CO$_2$ | (bar) | N$_2$ | W | C$_8$ | H$_2$ | CH$_4$ | C$_3$ | CO$_2$ |
| 48 | 237 | 19.0 | 0.8 | 1.2 | 10.4 | 13.0 | — | 5.3 | 18.1 | 46.7 | 0.8 | 1.1 | 0.02 | 0.03 | — | 0.03 |
| 49 | 258 | 20.1 | 0.6 | 0.9 | 16.2 | 7.8 | 2.6 | 1.7 | 18.9 | 49.9 | 0.4 | 0.8 | 0.4 | 0.05 | 0.2 | 0.4 |
| 50 | 240 | 20.9 | 1.4 | 1.9 | 18.3 | 7.4 | 2.6 | 0.4 | 19.2 | 46.0 | 0.5 | 0.6 | 0.03 | 0.01 | 0.06 | 0.01 |

| | Water Flow | $C_8$ Flow | Separation Factors | | | |
|---|---|---|---|---|---|---|
| Run | (kg · m$^{-2}$ · h$^{-1}$) | (kg · m$^{-2}$ · h$^{-1}$) | W/H$_2$ | W/CH$_4$ | W/C$_3$ | W/CO$_2$ |
| 48 | 1.1 | 10.1 | 353 | 308 | — | 116 |
| 49 | 0.6 | 7.2 | 37 | 171 | 15 | 82 |
| 50 | 0.8 | 5.1 | 226 | 273 | 17 | 15.5 |

EXAMPLE 6

This specific example illustrates that a decrease in the reaction water partial pressure inside a Fischer-Tropsch reactor operating with an iron based catalyst, results in an instant corresponding increase in the (H$_2$+CO) conversion levels per pass, and hence a dramatic increase in the Fischer-Tropsch reactor productivity.

The Anderson Fischer-Tropsch kinetic expression for an iron based Fischer-Tropsch catalyst (equation 11 as hereinafter described), was used to simulate the (H$_2$+CO) conversion level at different positions in the Fischer-Tropsch reactor and at different degrees of in-situ extraction of the reaction water. The reactor operating conditions were such that the temperature was 240° C., under 20 bar pressure and a feed composition of 66 vol % of hydrogen, and 34 vol % of carbon monoxide without a recycle. The cases that were studied were as follows:

Case A: No water removal (conventional Fischer-Tropsch reactors)

Case B: Membrane based removal of 50% of reaction water.

Case C: Membrane based removal of 66% of reaction water.

Case D: Membrane based removal of 90% of reaction water.

Figure 5:
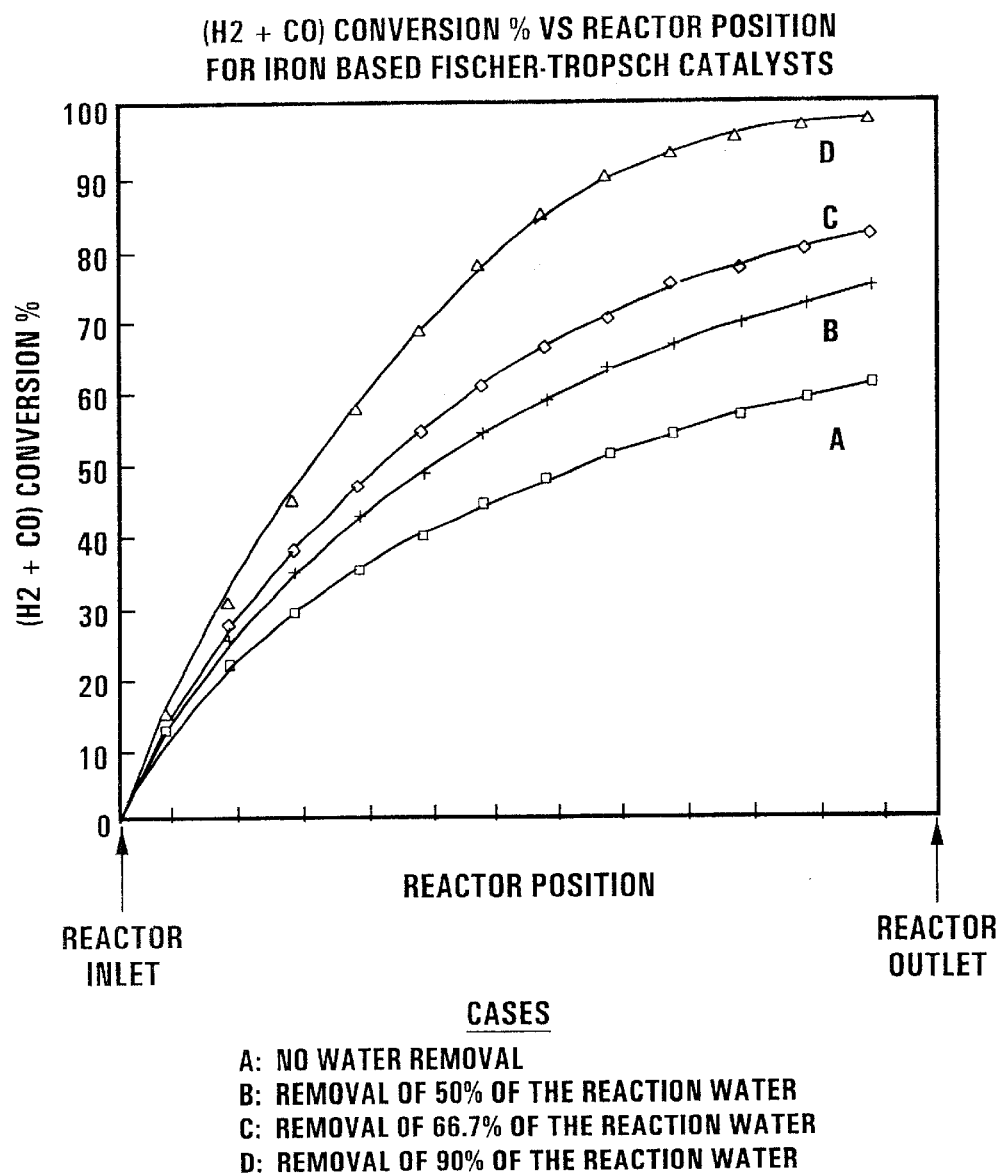
FIG. 5 shows a plot of ($H_2$+CO) conversion against reactor position for iron-based Fischer-Tropsch catalysts.

The results obtained are shown in FIG. 5 and in Table 9.

TABLE 9

($H_2$ + CO) Conversion Level Variation with Water Partial Pressure

| CASE | $P_{H2O}$ (bar) | ($H_2$ + CO) Conversion (%) |
|---|---|---|
| A | 4.77 | 58.8 |
| B | 3.60 | 72.2 |
| C | 2.95 | 79.8 |
| D | 0.92 | 95.9 |

FIG. 5 shows the per pass ($H_2$+CO) conversion percentage versus the position in the reactor. From this Figure, it is obvious that the removal of reaction water results in higher ($H_2$+CO) conversion levels, and therefore a higher reactor productivity.

If Cases A and B are compared, the removal of 50% of the reaction water results in an increase in the ($H_2$+CO) conversion level, from 58.8% to 72.2% per pass conversion. At the same time, the maximum partial pressure of water (at reactor outlet) decreases from 4.77 to 3.6 bar. This decrease in the partial pressure of water will result in a lower rate of catalyst reoxidation.

Calculations have shown that the volume occupied by the membrane inside the Fischer-Tropsch reactor, for the removal of about 50% of the reaction water is between 2.5 and 5%. This loss of reactor volume is more than compensated by the increase in the ($H_2$+CO) conversion level for Case B.

EXAMPLE 7

This specific example illustrates that a decrease in the reaction water partial pressure due to the presence of a zeolite membrane inside the Fischer-Tropsch reactor operating with a cobalt based catalyst, to values below a specific maximum (6 bar), permits the process to operate at a higher ($H_2$+CO) per pass conversion than could otherwise be practically achieved. Simultaneously the catalyst is exposed to a considerably reduced reoxidation threat, in stark contrast to the experience from the conventional reactor operating at the same high ($H_2$+CO) per pass conversions.

Yates and Satterfield's Fischer-Tropsch kinetic expression for a cobalt based catalyst (equation 13, as hereinafter described) was used to simulate the ($H_2$+CO) conversion level at different positions in the Fischer-Tropsch reactor and at different degrees of in-situ extraction of the reaction water. The reactor operating conditions were the same as those described in Example 6 above.

Figure 6:
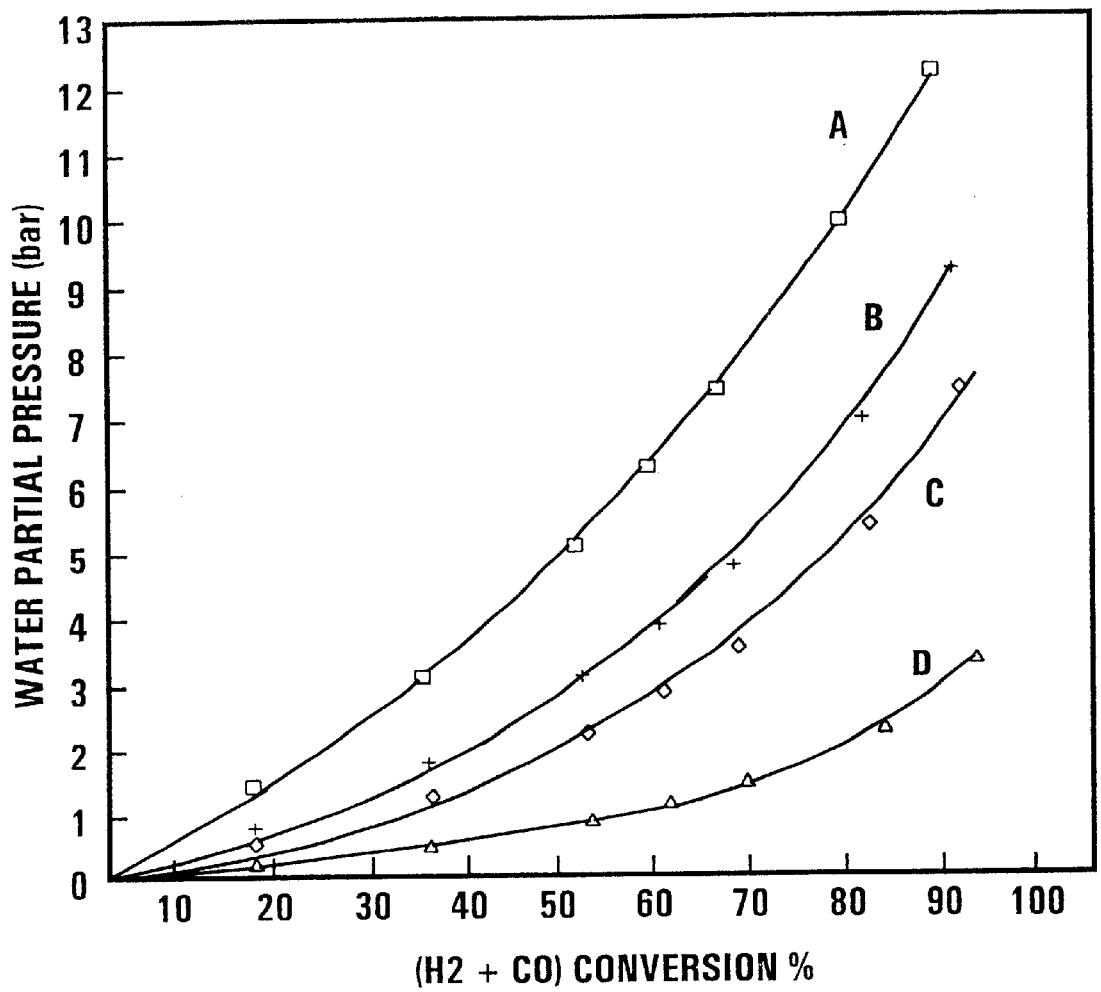
FIG. 6 shows a plot of partial pressure of water against ($H_2$+CO) conversion for a cobalt-based Fischer-Tropsch catalyst.

The results which disclose correlation between the partial pressure of water inside the reactor and the ($H_2$+CO) conversion percentage are shown in FIG. 6. As in FIG. 5, the zero ($H_2$+CO) conversion in FIG. 6 corresponds to the inlet of the reactor, while the maximum conversion for each case, corresponds to the reactor outlet.

As described hereinafter, a typical supported Fischer-Tropsch cobalt catalyst shows a high rate of water induced deactivation at high water partial pressures, typically 6 bar or higher. In order to maintain the catalyst activity, it is therefore necessary to operate at conditions that result in water partial pressures of less than 6 bar.

In a conventional Fischer-Tropsch reactor (no reaction water removed), operating at the typical reaction conditions used for this example, a water partial pressure of 6 bar is reached with a ($H_2$+CO) per pass conversion percentage of about 62%. This means that it is not practical to operate at per pass conversions higher than about 62%. Therefore, the kinetic advantage that exists for a cobalt based Fischer-Tropsch process cannot be transformed readily to high per pass ($H_2$+CO) conversion levels due to the negative effects of high partial pressures of water (>6 bar) on the catalyst's reoxidation rate.

An examination of FIG. 6 shows that a removal of 50% of the reaction water formed, has negligible influence on the degree of ($H_2$+CO) conversion is expected. The ($H_2$+CO) conversion percentage linked to a partial pressure of water of 6 bar, however, is now about 78%. This means that a Fischer-Tropsch reactor operating with a cobalt based catalyst, under the typical conditions described in the present example can increase its maximum and practical per pass conversion (in view of protecting the catalyst from reoxidation), from about 62% to approximately 78%. Higher degrees of water removal will result in higher maximum and practical per pass ($H_2$+CO) conversion, as shown in FIG. 6.

In the case of the iron based catalyst, water has, as also indicated hereinbefore, three notable negative effects:

It decreases the rate of the Fischer-Tropsch reaction.

It reoxidizes, and therefore deactivates, the catalyst.

In the case of a precipitated iron catalyst, reaction water lowers the mechanical strength of the catalyst particles.

Two of the most widely used kinetic expressions for iron based catalysts are the Anderson's and the Huff and Satterfield's expressions. They are normally represented as follows:

Anderson:

$$r_{FT} \alpha A e^{-E/RT} \frac{P_{H2} \cdot P_{CO}}{P_{CO} + a P_{H2O}} \quad \text{equation (11)}$$

Huff and Satterfield:

$$r_{FT} \alpha A e^{-E/RT} \frac{P_{H2}^2 \cdot P_{CO}}{P_{H2} \cdot P_{CO} + a P_{H2O}} \quad \text{equation (12)}$$

where:

$r_{FT}$=rate of the Fischer-Tropsch reaction

A=pre-exponential factor

E=activation energy

R=universal gas constant

T=temperature $P_i$=partial pressure of component i a=a constant

It is obvious from equations (11) and (12) that the partial pressure of water has a negative effect on the rate of the Fischer-Tropsch reaction. The higher the partial pressure of water, the lower the rate of the Fischer-Tropsch reaction.

Water also shows a negative effect on the stability of the active iron based Fischer-Tropsch catalysts. Higher partial pressures of water result in faster reoxidation rate of the iron catalyst. The active iron Fischer-Tropsch catalyst is in either a metallic or a carbided form. Once it is reoxidized by the water molecules, it becomes inactive for the Fischer-Tropsch reaction. The reoxidizing effect of water is well known by persons of ordinary skill in the Fischer-Tropsch field, and is well documented in literature.

The third negative effect of water (in this case, on a precipitated iron based Fischer-Tropsch catalyst) is the lowering of the mechanical strength of the Fischer-Tropsch catalyst particles. It has been repeatedly observed that the mechanical strength of the reduced/carbided precipitated iron Fischer-Tropsch catalyst is much higher than after reoxidation has taken place. Therefore, when the water reoxidizes the catalyst it also weakens it mechanically. In a slurry bed Fischer-Tropsch reactor, operating with a precipitated iron based catalyst, this mechanical weakening of the catalyst particles causes major problems in the separation of the catalyst particles from the hydrocarbon products in the wax range.

In the case of cobalt based Fischer-Tropsch catalysts, the partial pressure of water does not exhibit any negative effects on the rate of the Fischer-Tropsch reaction. This is evident from an analysis of the Yates and Satterfield Fischer-Tropsch reaction rate expression for cobalt based catalysts:

$$r_{FT} \alpha A e^{-E/RT} \frac{P_{H2} \cdot P_{CO}}{(1+aP_{CO})^2} \qquad \text{equation (13)}$$

where $r_{FT}$, A, E, R, T, Pi and a are as hereinbefore defined.

This expression, which is widely used by those involved in the Fischer-Tropsch field, does not include the partial pressure of water. Nevertheless, relatively high values for the partial pressure of water will result in the reoxidation of the active cobalt based Fischer-Tropsch catalyst, in a manner which is similar, although normally not as severe as is the case for the iron based Fischer-Tropsch catalysts. The reoxidizing effect of water on the cobalt based Fischer-Tropsch catalyst is also well known to those who are active in the Fischer-Tropsch field.

Based on the foregoing considerations, it is clear that the water, although a primary product of the Fischer-Tropsch reactions, has serious negative effects on iron and cobalt based Fischer-Tropsch processes.

Thus, the selective extraction of the reaction water from the Fischer-Tropsch reactors in accordance with the invention has a potential of offering considerable advantages in terms of the operation of the conventional reactors. Higher production rates per reactor volume and better catalyst protection from reoxidation and mechanical degradation during operation, and therefore longer catalyst lifetime will be obtained.

The Applicant has thus surprisingly found that zeolite based membranes can be successfully utilized for the selective removal of water from a hydrocarbon species and a fraction of permanent gas mixture that is maintained under Fischer-Tropsch reaction conditions.

The separation devices used in the process of the invention can also be made in accordance with the procedures outlined in J. Membrane Science, 149 (1998) pg 99–114, "Synthesis, characterization ahd separation properties of a composite mordenite/ZSM-5/chabazite hydrophilic membrane", by E. Piera, M. A. Salomon, J. Coronas, M. Menendez and J. Santamaria.

What is claimed is:

1. A process for producing hydrocarbons, which process comprises:

allowing reactants forming part of a reaction medium in a reaction zone, to react at reaction conditions so as to form primary hydrocarbon products, with water being formed as a by-product; and allowing by-product water, on formation thereof under the reaction conditions, to permeate through a membrane that selectively removes water from the reaction medium, thereby to be separated from the reaction medium.

2. A process according to claim 1, wherein the reactants are in gaseous form and comprise carbon monoxide and hydrogen, with a particulate Fischer-Tropsch catalyst also forming part of the reaction medium, and with the reaction conditions being such that the carbon monoxide and hydrogen react in the presence of the Fischer-Tropsch catalyst, to produce, as the primary hydrocarbon products, liquid Fischer-Tropsch derived hydrocarbon product(s) and/or gaseous Fischer-Tropsch derived product(s), in accordance with a simplified Fischer-Tropsch reaction equation (1):

$$CO+(1+x)H_2 \rightarrow CH_{2x}+H_2O \qquad (1).$$

3. A process according to claim 2, wherein the reaction zone is provided by a slurry bed reactor, the slurry bed of which comprises liquid hydrocarbon products, gaseous hydrocarbon products, water, gaseous reactants, and catalyst particles, with the membrane thus being located within the slurry bed, and with the reaction medium also comprising liquid hydrocarbon products, gaseous hydrocarbon products, water, gaseous reactants and catalyst particles.

4. A process according to claim 2, wherein the reaction zone is provided by a fluidized bed reactor, the fluidized bed of which comprises gaseous hydrocarbon products, gaseous reactants, water, and catalyst particles, with the membrane thus being located within the fluidized bed, and with the reaction medium also comprising gaseous hydrocarbon products, water, gaseous reactants and catalyst particles.

5. A process according to claim 1, wherein the membrane is supported by a water-permeable support such that the membrane has a water inlet side and a water outlet side, with the by-product water thus entering the membrane through its water inlet side, permeating through the membrane, and exiting the membrane through its water outlet side, and with the support and the membrane thus forming a water separation device.

6. A process according to claim 5, which includes passing an inert sweep gas along the support in proximity to the water outlet side of the membrane, to entrain water which permeates through the membrane, thereby to provide a driving force for water permeation through the membrane.

7. A process according to claim 6, wherein the support is of tubular form with the membrane being provided on the inner or the outer surface of the tubular support, and with the sweep gas passing through the inside of the membrane.

8. A process according to claim 7, wherein the sweep gas enters the reaction zone through a conduit connected to the inside of the tubular support at or near one end thereof, passes through the support, and exits the reaction zone through another conduit leading from the support at or near another end thereof, out of the reaction zone.

9. A process according to claim 5, wherein the membrane is of porous zeolitic material selected from mordenite, ZSM-5, zeolite A, and chabazite.

10. A process according to claim 5, wherein the water-permeable support is of porous stainless steel.

* * * * *